United States Patent

Iwasaki et al.

Patent Number: 5,817,880
Date of Patent: Oct. 6, 1998

[54] INTERMEDIATE ALCOHOL COMPOUND

[75] Inventors: Tomonori Iwasaki; Kazunori Tsushima, both of Sanda; Takashi Furukawa, Takarazuka; Takao Ishiwatari, Minoo; Toru Tsuchiya, Takarazuka; Mikako Nakamachi, Minoo, all of Japan

[73] Assignee: Sumitomo Chemical Company, Limited, Osaka, Japan

[21] Appl. No.: 818,747

[22] Filed: Mar. 14, 1997

Related U.S. Application Data

[62] Division of Ser. No. 492,980, Jun. 21, 1995, Pat. No. 5,653,990.

[30] Foreign Application Priority Data

Jun. 22, 1994 [JP] Japan .................................. 06-140003

[51] Int. Cl.⁶ .......................... C07C 49/597; C07C 35/06
[52] U.S. Cl. ........................................... 568/380; 568/838
[58] Field of Search ...................................... 568/380, 838

[56] References Cited

U.S. PATENT DOCUMENTS

| | | |
|---|---|---|
| 4,496,586 | 1/1985 | Matsui et al. . |
| 5,550,258 | 8/1996 | Iwasaki et al. ............................ 549/78 |

FOREIGN PATENT DOCUMENTS

| | | |
|---|---|---|
| 643037 | 3/1995 | European Pat. Off. . |
| 52-148045 | 8/1977 | Japan . |
| 52093746 | 8/1977 | Japan . |
| 56-065459 | 6/1981 | Japan . |
| 57-067537 | 4/1982 | Japan . |

OTHER PUBLICATIONS

Patent Abstracts of Japan—vol. 1 No. 149 (C–031)(3266) Nov. 30, 1977 & JP–A–52 093 746 (Sankyo) Jun. 8, 1977—*abstract*.

Chem. Abst. Tenth Collective Index, Chemical Substances 1982, American Chemical Society p. 17591cs, column 2 and *p. 17595cs, column 1: "2,2–dimethyl–3–(2–methyl–1–propenyl) cyclopropanecarboxylic acid, 3–(iodomethyl)2–methyl–4–oxo–2–cyclopenten–1–ylester".

Pesticide Science, vol. 40, No. 4, Apr. 1994, pp. 307–312 T. Ando et al. "Insecticidal activity of new fluorinated pyrethroids and their stability toward chemical oxidation and photoreaction" *p. 309, compounds 9 and 10; p. 310, Table 1*.

Chemical Abstracts, vol. 96, No. 1, Jan. 4, 19982, Columbus Ohio, US; abstract No. 6253p, "Cyclopropanecarboxylate esters as insecticides" p. 565; column 1; *abstract & JP–A–81 075 460 (Sumitomo Chemical).

*Primary Examiner*—Gary Geist
*Assistant Examiner*—Rosalynd Keys
*Attorney, Agent, or Firm*—Birch, Stewart, Kolasch & Birch, LLP

[57] ABSTRACT

There is provided an intermediate alcohol ester compound represented by the formula VII:

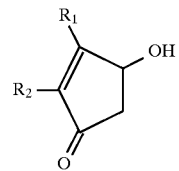

wherein $R_1$ is a methyl group or a hydrogen atom; $R_2$ is a $C_{2-4}$ alkyl group; substituted with two or more fluorine atoms.

9 Claims, No Drawings

INTERMEDIATE ALCOHOL COMPOUND

This application is a divisional of application Ser. No. 08/492,980, filed on Jun. 21, 1995, U.S. Pat. No. 5,653,990, the entire contents of which are hereby incorporated by reference.

FIELD OF THE INVENTION

The present invention relates to an ester compound, an agent for controlling noxious organisms containing the same as an active ingredient, and a production intermediate thereof.

The present inventors have studied intensively in order to find a compound having an excellent effect for controlling noxious organisms. As a result, it has been found that an ester compound represented by the following formula I has an excellent effect for controlling noxious organisms and, at the same time, an alcohol compound represented by the formula VII described hereinafter is a useful intermediate in the production of the ester compound, thus the present invention has been accomplished.

SUMMARY OF THE INVENTION

That is, the present invention provides an ester compound represented by the formula I:

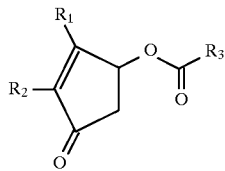

wherein $R_1$ is a methyl group or a hydrogen atom; $R_2$ is a $C_{1-6}$ haloalkyl group; and $R_3$ is a pyrethroid acid residue (which excludes a carboxyl group) (hereinafter referred to as a "present compound"), an agent for controlling noxious insects containing the same as an active ingredient and, a production intermediate thereof.

PREFERRED EMBODIMENT OF THE INVENTION

In the present compound I the $C_{1-6}$ haloalkyl group for $R_2$ includes, for example, $C_{2-4}$ alkyl groups which may be substituted with a fluorine atom or atoms such as 2,2,2-trifluoroethyl group, 2,2-difluoroethyl group, pentafluoroethyl group, 2-fluoroethyl group and 3-fluoropropyl group.

The pyrethroid acid residue $R_3$ may be any residue that constitutes a pyrethroid acid of an active pyrethroid ester insecticide and is not specifically limited, and examples thereof include a group represented by the formula II:

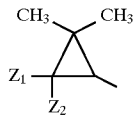

wherein $Z_1$ is a hydrogen atom or a methyl group; and $Z_2$ is a hydrogen atom, a $C_1$–$C_6$ alkyl group which may be substituted with a halogen atom or atoms, a $C_1$–$C_6$ alkoxy group which may be substituted with a halogen atom or atoms, a ($C_1$–$C_6$ alkoxy)methyl group which may substituted be with a halogen atom or atoms, a ($C_1$–$C_6$ alkoxy)ethyl group which may be substituted with a halogen atom or atoms, a $C_2$–$C_4$ alkenyloxy group which may be substituted with a halogen atom or atoms, a $C_2$–$C_4$ alkynyloxy group which may be substituted with a halogen atom or atoms, a ($C_2$–$C_4$ alkenyl)oxymethyl group which may be substituted with a halogen atom or atoms or a ($C_2$–$C_4$ alkynyl) oxymethyl group which may substituted with a halogen atom or atoms; $Z_2$ is a group of the formula III:

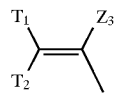

wherein $Z_3$ is a hydrogen atom or a halogen atom; and $T_1$ and $T_2$ are the same or different and each indicate a hydrogen atom, a halogen atom, a $C_1$–$C_3$ alkyl group which may substituted with a halogen atom or atoms, a cyano group, a phenyl group which may substituted with a halogen atom or atoms, a ($C_1$–$C_4$ alkoxy)carbonyl group which may substituted with a halogen atom or atoms, or $T_1$ and $T_2$ bonded together at their terminal-and indicate a $C_3$–$C_6$ cycloalkyl group; $Z_2$ is a group of the formula IV:

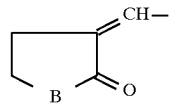

wherein B is an oxygen atom or a sulfur atom; $Z_2$ is a group of the formula V:

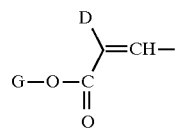

wherein D is a hydrogen atom or a halogen atom; and G is a $C_1$–$C_6$ alkyl group which may be substituted with a halogen atom or atoms, a $C_3$–$C_5$cycloalkyl group or a phenyl group which may be substituted with a halogen atom or atoms; or $R_3$ is a group of the formula VI:

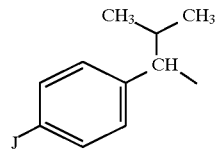

wherein J is a halogen atom, a $C_1$–$C_6$ alkyl group which may be substituted with a halogen atom or atoms or a $C_1$–$C_6$ alkoxy group which may be substituted with a halogen atom or atoms.

In the formulas for the present compound above, examples of the halogen atom include a fluorine atom, a chlorine atom and a bromine group, etc., examples of the alkyl group include a methyl group, an ethyl group and a propyl group, etc., examples of the alkenyl group include an allyl group, etc, examples of the alkynyl group include a propargyl group, etc., and examples of the alkoxy group include a methoxy, ethoxy and propoxy group, etc.

For the group $Z_2$ in the formula II above, the $C_1$–$C_6$ alkyl group which may be substituted with a halogen atom or atoms includes a methyl group, the $C_1$–$C_6$ alkoxy group which may be substituted with a halogen atom or atoms includes $C_2$–$C_5$ alkoxy groups such as a propoxy group, a butoxy group, the $C_2$–$C_4$ alkenyloxy group which may be substituted with a halogen atom or atoms includes an allyloxy group, a $C_2$–$C_4$ alkynyloxy group which may be substituted with a halogen atom or atoms includes a propargyloxy group, the ($C_2$–$C_4$ alkenyl)oxymethyl group which may be substituted with a halogen atom or atoms includes an allyoxymethyl group, and the ($C_2$–$C_4$ alkynyl)oxymethyl group which may substituted with a halogen atom or atoms includes propargyloxymethyl group.

The $C_3$–$C_6$ cycloalkyl group formed from $T_1$ and $T_2$ in formula III includes a cyclopropyl group, a cyclobutyl group, a cyclopentyl group or a cyclohexyl group.

In Formula V the $C_1$–$C_6$ alkyl group which may be substituted with a halogen atom or atoms for G includes a $C_1$–$C_3$ alkyl groups which may be substituted with a fluorine atom or atoms, such as an ethyl group, etc and the $C_3$–$C_5$ cycloalkyl group includes a cyclopropyl group etc.

For the group J in Formula VI the $C_1$–$C_6$ alkyl group which may be substituted with a halogen atom or atoms includes a trifluoromethyl group, and difluoromethyl group, etc. and the $C_1$–$C_6$ alkoxy group which may be substituted with a halogen atom or atoms includes a trifluoromethoxy group and a difluoromethoxy group, etc.

In the present compound, the $C_{1-6}$ haloalkyl groups for $R_2$ are preferably a $C_{2-4}$ alkyl group substituted with a fluorine atom or atoms, among which a 2,2,2-trifluoroethyl group is particularly preferred.

In the present compound, when $R_2$ is a secondary $C_{1-6}$ haloalkyl group, $R_1$ is preferably a hydrogen atom, and when $R_2$ is a primary $C_{1-6}$ haloalkyl group, $R_1$ is preferably a methyl group.

In the present compound, preferred examples of the pyrethroid acid residue represented by $R_3$ (which excludes a carboxyl group) include $Q_1$ to $Q_{27}$ described in the formulas X and XI described hereinafter.

The present compound can be produced, for example, by the following process.
(Production process A)
A process for producing the present compound, comprising reacting an alcohol compound represented by the formula VII:

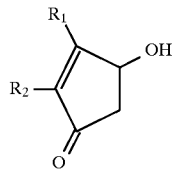

wherein $R_1$ and $R_2$ are as defined above with a carboxylic acid represented by the formula VIII:

$R_3$—COOH wherein $R_3$ are as defined above or a reactive derivative thereof.

Examples of the reactive derivative of the carboxylic acid include acid halide compounds, acid anhydrides and the like.

It is preferred that the reaction is conducted in an inert solvent in the presence of a suitable condensing agent or a base, if necessary. Examples of the condensing agent include dicyclohexylcarbodiimide (DCC), 1-ethyl-3-(3-dimethylaminopropyl)carbodiimide hydrochloride (WSC) and the like.

Examples of the base to be used include organic bases such as triethylamine, pyridine, 4-dimethylaminopyridine, diisopropylethylamine and the like. Examples of the solvent to be used include hydrocarbons such as benzene, toluene, hexane, etc.; ethers such as diethyl ether, tetrahydrofuran, etc.; halogenated hydrocarbons such as dichloromethane, 1,2-dichloroethane, etc.

The reaction temperature can be preferably within a range from –20° C. to 10 the boiling point of the solvent used for the reaction or 100° C., more preferably from –5° C. to the boiling point of the solvent used for the reaction or the temperature up to 100° C. The molar ratio of the alcohol compound represented by the formula VII to carboxylic acid represented by the formula VIII or the reactive derivative thereof to be used can be optionally set, but is advantageous to set at an equimolar ratio or the ratio similar to the equimolar ratio. The condensing agent or base can be used in an amount within a range from an equimolar amount to an excessive amount, preferably from an equimolar amount to 5 mols, based on 1 mol of the alcohol compound of the formula VII.

After the completion of the reaction, the reaction solution can be subjected to a normal workup treatment such as extraction with organic solvent, concentration, etc. to give the objective present compound. If necessary, it may be purified by normal operations such as chromatography, distillation, recrystallization and/or the like.

The present compounds have stereoisomers (R/S) and geometrical isomers (cis/trans and E/Z), and all stereoisomers and geometrical isomers and a mixture thereof which have an activity for controlling noxious organisms are included in the present invention.

In the above production process A, an optically active compound can be obtained from optically active materials without causing racemization, i.e. with retention of stereoisomerism.

In the production process A, examples of the alcohol compound represented by the formula VII to be used as the raw compound include the following compounds;

(RS)-3-(2-fluoroethyl)-2-methyl-4-oxo-2-cyclopentenol,
(S)-3-(2,2,2-trifluoroethyl)-2-methyl-4-oxo-2-cyclopentenol,
(RS)-3-(3,3-difluoropropyl)-2-methyl-4-oxo-2-cyclopentenol,
(RS)-3-(pentafluoroethyl)-2-methyl-4-oxo-2-cyclopentenol,
(RS)-3-(2,2,2-trifluoroethyl)-2-methyl-4-oxo-2-cyclopentenol,
(RS)-3-(3,3,3-trifluoropropyl)-2-methyl-4-oxo-2-cyclopentenol,
(RS)-3-(2,2-difluoroethyl)-2-methyl-4-oxo-2-cyclopentenol,
(RS)-3-(2-chloroethyl)-2-methyl-4-oxo-2-cyclopentenol,
(RS)-3-(2-chloro-2,2-difluoroethyl)-2-methyl-4-oxo-2-cyclopentenol.

The alcohol compound represented by the formula VII can be produced, for example, according to the method described in Japanese Patent Kokai (Laid-open) No. 57-67537. More definitely, ii can be produced, for example, by the method shown in following reaction scheme IX.

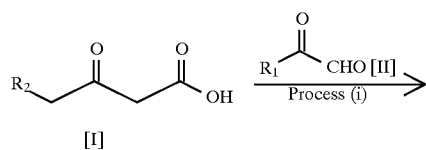

-continued

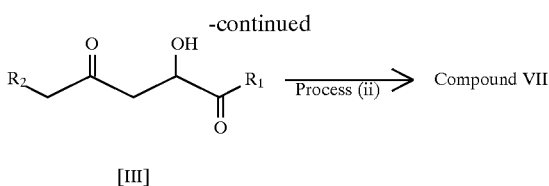

[III]

wherein $R_1$ and $R_2$ are as defined above.

Hereinafter, the processes [i] and [ii] will be explained.

Process (i): A ketocarboxylic acid compound represented by the formula [I] is reacted with a glyoxal derivative of the formula [II] in an aqueous alkaline solution or a mixed solvent of the aqueous alkaline solution and an inert solvent at a temperature within a range normally from 10° C. to a boiling point of the solvent to be used or 100° C., preferably from 20° C. to a boiling point of the solvent to be used or 100° C., for 10 minutes to 48 hours. It is advantageous to react the reaction solution at a pH range of from 7 to 9. Examples of the inert solvent to be used optionally include ethers such as diethyl ether, tetrahydrofuran, etc.; halogenated hydrocarbons such as dichloromethane, etc.; hydrocarbons such as benzene, toluene, etc.

The molar ratio of the ketocarboxylic compound of the formula [I] to glyoxal derivative of the formula [II] to be used for the reaction can be optionally set, but is advantageous to set at an equimolar ratio or the ratio similar to the equimolar ratio.

Process (ii): After removing the solvent, the residue was reacted in an aqueous alkaline solution (pH is not less than 10, preferably 13 to 14) at a temperature within a range normally from −50° C. to 20° C., preferably from −20° C. to 5° C. for 30 minutes to 48 hours. After the completion of the reaction, the reaction solution can be subjected to a normal workup such as extraction with organic solvent, concentration, etc. to isolate the objective compound. If necessary, it may be purified by normal operations such as chromatography, distillation and the like.

The ketocarboxylic acid compound represented by the formula [I] can be produced, for example, by the method represented by the following reaction scheme X.

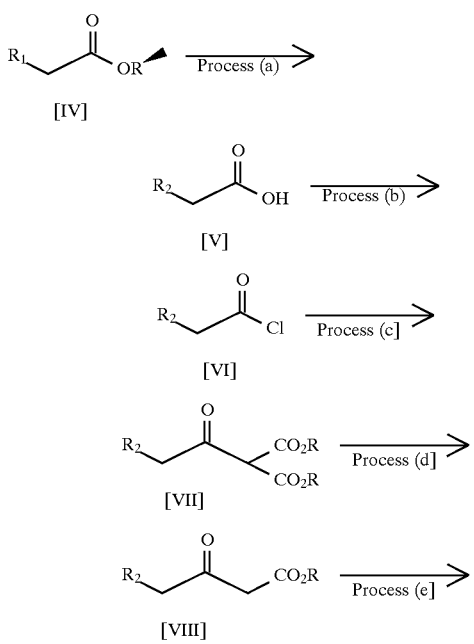

-continued

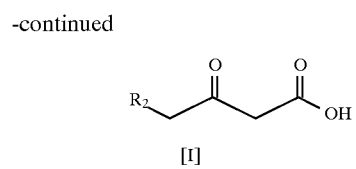

[I]

wherein R and R' are the same or different and indicate a $C_{1-4}$ alkyl group (e.g. methyl group, ethyl group, etc.); and $R_2$ is as defined above.

Hereinafter, the processes (a) to (e) will be explained.

The step (a) of hydrolyzing an ester represented by the formula [IV] to produce a carboxylic acid represented by the formula [V] will be explained.

Usually, a base such as hydroxides of alkali metals (e.g. sodium hydroxide, potassium hydroxide, etc.), hydroxides of alkali earth metals (e.g. barium hydroxide, etc.), carbonates of alkali metals (e.g. potassium carbonate, sodium carbonate, etc.) is used in an amount of usually 1 to 10 equivalents, preferably 1.2 to 5 equivalents, based on the amount of an ester of the formula [IV] and the base is reacted with the ester in a protonic solvent (e.g. water, methanol, ethanol, ethylene glycol, etc.) at a temperature within a range usually from −10° C. to a boiling point of the solvent to be used or 100° C., preferably from 0° C. to 50° C., for 30 minutes to 48 hours. After completion of the reaction, the reaction solution can be subjected to a normal workup such as extraction with organic solvent, concentration, etc. to isolate the objective present compound. If necessary, it may be purified by normal operations such as distillation and the like.

Hereinafter, the process (b) of halogenating a carboxylic acid represented by the formula [V] to produce a carboxylic acid halide represented by the formula [VI] will be explained.

Usually, the carboxylic acid of the formula [V] is reacted with a halogenating agent directly or in a hydrocarbon such as hexane, pentane, etc. Examples of the halogenating agent to be used include inorganic chlorides such as phosphoryl chloride, thionyl chloride, etc.; organic chlorides such as oxalic chloride, etc. If necessary, catalysts such as pyridine, triethylamine, N, N-dimethylformamide, hexamethylphosphoric triamide, etc. may be added in an amount of 0.01 to 1 mol, based on 1 mol of the carboxylic acid of the formula [V]. The reaction temperature may be usually within a range from 0° C. to a boiling point of the solvent to be used or 150° C. The molar ratio of the raw material and the halogenating agent to be used for the reaction can be optionally set, but is advantageous to set at an equimolar ratio or the ratio similar to the equimolar ratio. After the completion of the reaction, the reaction solution can be subjected to a normal workup-treatment such as extraction with an organic solvent, concentration, etc. to isolate the compound. If necessary, it may be purified by usual operations such as distillation and the like.

Hereinafter, the process (c) of reacting the carboxylic acid halide represented by the formula [VI] with diethyl malonate to produce a compound represented by the formula [VII] will be explained.

Usually, the carboxylic acid halide of the formula [VI] is reacted with diethyl malonate directly or in an inert solvent in the presence of alcohols such as ethanol, methanol, etc. and suitable metals. Example s of the metal to be used include alkaline earth metals such as magnesium, etc., alkaline metals such as lithium, etc. Examples of the solvent, used if necessary, include hydrocarbons such as benzene, xylene, toluene, etc. and ethers such as diethyl, ether, tetrahydrofuran, dioxane, etc. The amount of the diethyl malonate, alcohol and metal can be optionally set, respectively, and they are preferably used in an amount of 1.2 to 5 equivalents, based on the amount of the carboxylic acid halide of the formula [VI], respectively. The reaction temperature may be usually within a range from −30° C. to a boiling point of the solvent to be used or 150° C. After the completion of the reaction, the reaction solution can be subjected to a normal workup such as extraction with organic solvent, concentration, etc. to isolate the objective compound. If necessary, it may be purified by normal operations such as chromatography, distillation, recrystallization and the like.

Hereinafter, the process (d) of hydrolyzing the compound represented by the formula [VII], followed by decarboxylation to obtain a ketoester compound represented by the formula [VIII] will be explained.

When the reaction is conducted under a basic condition, the ketoester compound of he formula [VII] is usually reacted in protonic solvents such as water, methanol, ethanol, ethylene glycol, etc. or a mixed solvent thereof at a temperature within a range usually from 0° C. to a boiling point of the solvent to be used, preferably not less than 30° C. for 10 minutes to 48 hours in the presence of hydroxides of alkaline metals, such as sodium hydroxide, potassium hydroxide, etc., hydroxides of alkaline earth metals, such as barium hydroxide, etc., carbonates of alkaline metals, such as potassium carbonate, sodium carbonate, etc. The molar ratio of the raw material to the base to be used for the reaction can be optionally set, but is advantageous to set at an equimolar ratio or the ratio similar to the equimolar ratio.

When the reaction is conducted under the acidic condition, the ketoester compound of the formula [IV] is usually reacted in water or a mixed solvent of water and alcohols (e.g. ethanol, methanol, etc.) or ethers (e.g. dioxane, tetrahydrofuran, etc.) at a temperature within a range usually from 0° C. to a boiling point of the solvent to be used, preferably not less than 30° C. for 10 minutes to 48 hours in the presence of acids such as p-toluenesulfonic acid, trifluoroacetic acid, hydrochloric acid, etc. The molar ratio of the raw material and acid to be used for the reaction can be optionally set, but is preferably used in the amount of 0.0001 to 1 moles. After the completion of the reaction, the reaction solution can be subjected to a normal workup such as extraction with organic solvent, concentration, etc. to isolate the objective compound. If necessary, it may be purified by normal operations such as chromatography, distillation and the like.

The process (e) of hydrolyzing a ketoester compound of the formula [VIII] to produce a ketocarboxylic compound represented by the formula [I] can be conducted according to the same manner as that described in the process (a).

Examples of noxious insects against which the present compound exhibits a control effect include the followings:

Hemiptera:
Delphacidae (planthoppers) such as *Laodelphax striatellus, Nilaparvata lugens* and *Soqatella furcifera;*
Cicadelloidea (leafhoppers) such as *Nephotettix cincticeps Recilia dorsalis* and *Nerphotettix virescens,* Aphidoidea (aphids), plant bugs such as Pentatomidae, Coreidae, Alydidae, Tingidae (lace bugs), and Miridae, Aleyrodidae, Coccoidea (scale insects), Psyllidae (jumping piant-lices), etc.;

Lepidoptera:
Pyralidae such as *Chilo suppressalis* and *Cnaphalocrocis medinalis,* Noctuidae (owlet moths) such as *Spodoptera litura, Pseudaletia separata,* and *Mamestra brassicae, Heliothis* moths, Agrotis moths such as *Agrotis ipsilon* and Agrotis segetum (turnip moth), Pieridae such as *Pieris rapae crucivora,* Tortricidae (bell moths), carposinidae, Lyonetiidae, Lymantriidae, *Plutella xylostella, Tinea translucens, Tineola bisselliella,* etc.;

Diptera:
Culex (house mosquitoes) such as *Culex pipiens pallens* and *Culex tritaeniorhynchus,* Aedes such as *Aede albopictus* and *Aedes aegypti,* Anopheles such as *Anopheles sinensis,* Chironomidae (midges), Muscidae such as Musca domestica (house fly) and *Muscina stabulans, Fannia canicularis,* Calliphoribae (blow fries), Sarcophagidae (flesh flies), Anthomyiidae such as *Delia Platura and Delia antiqua,* Thphritidae (fruit flies), Drosophilidae, Psychodidae (moth flies), Tabanidae (deer flies), Simuliidae (black flies), Stomoxyidae, etc.;

Coleoptera (beetles):
Diabrotica (corn rootworms) such as *Diacrotica virgifera* and *Diabrotica undecimpunctata,* Scarabaeidae such as *Anomala cuprea* and *Anomala rufocuprea,* Curculionidae (snout beetles) such as *Sitophilus zeamais* (grain weevils) and *Lissorhoptrus oryzophilus,* Tenebrionidae (darkling beetles) such as *Neatus ventralis, Tenebrio molitor* and *Triboiium castaneum,* Chrysomelidae (leaf beetles) such as *Aulacophora femoralis* and *Phylotreta striolata,* Anobiidae (death-watch beetles), Coccinellidae (ladybird beetles) such as *Epilachna vigintioctopunctata,* Lyctidae (powder-post beetles), Bostrychidae Ceranbycidae, *Paederus fuscipes, etc.;*

Blattaria (cockroaches):
*Blattella germanica, Periplaneta fuliainosa, Periplaneta americana, Periplaneta brunnea, Blatta orientalis,* etc.;

Thysanoptera (thrips):
*Thrips palmi, Thrips tabaci, Thrips hawaiiensis,* etc.;

Hymenoptera:
Formicidae (ants), Vespidae (hornets), Bethylidae (bethylid wasps), Tenthredinidae (sawflies) such as *Athalia japionica* (cabbage sawfly), etc.;

Orthoptera:
Gryllotalpidae (mole crickets), Acrididae (grasshoppers), etc.;

Siphonaptera (fleas):
*Purex irritans,* etc.;

Anoplura (sucking lice):
*Pediculus humanus, Pthirus pubis,* etc.;

isoptera (termites):
noxious insects such as *Reticulitermes speratus, Coptotermes formosanus,* etc.;

Tetranychidae (spider mites):
*Tetranychus cinnabarinus, Tetranychus urticae, Tetranychus kanzawai, Panonychus citri, Panonychus ulmi,* etc.;

Ixodidae (ticks):
*Boophilus microplus;*

House dust mites:
noxious mites such as Acaridae, Pyroglyphidae, Cheyletidae, Macronyssidae, etc.;

Nematoda (soil nematodes):
root-lesion nematodes, cyst nematodes, root-knot nematodes, etc.; and Nematoda (nematodes):
   *Bursaphelenchus xylophilus* (pine wood nematode), etc.

When the present compound is used as an active ingredient of an agent for controlling noxious organisms, it is usually mixed with solid carriers, liquid carriers, gaseous carriers, baits, etc. to formulate. Alternatively, a base material of a mosquito-coil or an electric mosquito-mat for electric heating fumigation is impregnated with the present compound. Surfactants and other auxiliary agents for formulation may be optionally added to the present compound. Examples of the formulation for the present compound include oil solutions, emulsifiable concentrates, wettable powders, flowables such as water suspensions and emulsions, granules, dusts, aerosols, heating smoke formulations such as mosquito-coils, mosquito-mats, or non-mats for electric heating fumigation, self-combustion type smoke formulations, chemical reaction type smoke formulations, heating smoke formulations such as a porous ceramic fumigant, non-heating transpiration formulations such as volatile agents applied on resin or paper, fogging agents, ULV agents, poison bait and the like.

These formulations usually contain the present compound as the active ingredient in an amount of 0.001 to 95% by weight.

Examples of the solid carrier used for the preparation include fine powders or particulates such as clays (e. g. kaolin clay, diatomaceous earth, synthetic hydrated siliconoxide, bentonite, Fubasami clay, acid clay, etc.), talcs, ceramics, other inorganic minerals (e.g. sericite, quartz, sulfur, active carbon, calcium carbonate, hydrated silica, etc.), commercial fertilizers (e.g. ammonium sulfate, ammonium phosphate, ammonium nitrite, urea, ammonium chloride, etc.). Examples of the liquid carrier include water, alcohols (e.g. methanol, ethanol, etc.), ketones (e.g. acetone, methyl ethyl ketone, etc.), aromatic hydrocarbons (e.g. benzene, toluene, xylene, ethylbenzene, methylnaphthalene, etc.), aliphatic hydrocarbons (e.g. hexane, cyclohexane, kerosene, gas oil, etc.), esters (e.g. ethyl acetate, butyl acetate, etc.), nitriles (e.g. acetonitrile, isobutylonitrile, etc.), ethers (e.g. diisopropyl ether, dioxane, etc.), acid amides (e.g. N,N-dimethylformamide, N,N-dimethylacetamide, etc.), halogenated hydrocarbons (e.g. dichloromethane, trichloroethane, carbon tetrachloride, etc.), dimethyl sulfoxide, vegetable oils (e.g. soybean oil, cottonseed oil, etc.) and the like. Examples of the gaseous carrier, i.e. propellant include flon gas, butane gas, LPG (liquefied petroleum gas), dimethyl ether, carbon dioxide gas and the like.

Examples of the surfactant include alkyl sulfate, alkyl sulfonate, alkyl aryl sulfonate. alkyl aryl ethers and polyoxyethylene alkyl aryl ether, polyoxyethylene glycol ethers, polyhydroxy alcohol esters, sugar alcohol derivatives and the like.

Examples of the auxiliary agent for formulation include stickers and dispersants, such as casein, gelatin, polysaccharides (e.g. starch, gum arabic, cellulose derivative, alginic acid, etc.), lignin derivatives, bentonite, saccharides, synthetic water-soluble polymers (e.g. polyvinyl alcohol, polyvinyl pyrrolidone, polyacrylic acids, etc.). Examples of the stabilizer include PAP (acid isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids or esters thereof.

Examples of the base material of the mosquito-coils include a mixture of wood powder such as pyrethrum marc, powder of Machilus thunbergii sieb et Zucc. and a binding agent like starch or gluten.

Examples of the base material of the mosquito-mat for electric heating fumigation include a plate of compacted fibrils of cotton linters or a mixture of pulp and cotton linters Examples of the base material of the self-combustion type smoke formulation include combustion exothermic agents (e.g. nitrate, nitrite, guanidine salt, potassium chlorate, nitrocellulose, ethyl cellulose, wood flour, etc.), pyrolysis stimulants (e.g. alkaline metal salt, alkaline earth metal salt, bichromate, chromate, etc.), oxygen suppliers (e.g. potassium nitrate, etc.), a combustion assistant (e.g. melamine, wheat starch, etc.), bulking agents (e.g. diatomaceous earth, etc.), binders (e.g. synthetic starch, etc.) and the like.

Examples of the base material of the chemical reaction type smoke formulation include exothermic agents (e.g. sulfide, polysulfide, water sulfide and hydrated salt of alkali metal, calcium oxide, etc.), catalysts (e.g. carbonaceous substance, iron carbide, activated clay, etc.), organic foaming agents (e.g. azodicarbonamide, benzenesulfonyl hydrazide, dinitrosopentamethylenetetramine, polystyrene, polyurethane, etc.), fillers (e.g. natural fiber fragment, synthetic fiber fragment, etc.) and the like.

Examples of the base material of non-heating transpiration formulation include thermoplastic resin, filter paper, Japanese paper and the like.

Examples of the base material of the poison bait include bait components such as grain powder, vegetable oil, sugar, crystalline cellulose, etc.; antioxidants such as dibutylhydroxytoluene, nordihydroguaiaretic acid, etc.; preservatives such as dehydroacetic acid, etc.; substances for preventing erroneous ingestion such as red pepper powder, etc.; attractant flavors such as cheese flavor, onion flavor, peanut oil, etc.

Flowabies (water suspension or emulsion) can be obtained by finely dispersing 1 to 75% by weight of the compound as an active ingredient in water containing 0.5 to5% by weight of a dispersing agent, 0 to 10% by weight of a suspension auxiliary (e.g. protective colloid, compound imparting thixotropic properties, etc.) and 0 to 10% by weight of an auxiliary agent (e.g. defoamer, rust preventive, stabilizer, spreading agent, penetration auxiliary, antifreezing agent, antibacterial agent, antifungal substance, etc.). It is also possible to formulate into a suspension in oil by using an oil in which the compound is hardly dissolved in place of water. As the protective colloid, for example, there can be used gelatin, casein, gums, cellulose ether, polyvinyl alcohol and the like. Examples of the compound imparting thixotropic properties include bentonite, aluminum magnesium silicate, xanthangum, polyacrylic acid and the like.

The formulation thus obtained is used as prepared or after diluted with water. The formulations may be used after mixed with other insecticides, acaricides, nematicides, soil insect pest control agents, fungicides, herbicides, plant growth regulators, synergists, fertilizers, soil conditioners and the like, or used simultaneously with them.

Examples of the insecticide, nematicide and acaricide include organophosphorous compounds such as fenitrothion [O,O-dimethyl O-(3-methyl-4-nitrophenyl) phosphorothioate],
fenthion [O,O-dimethyl O-(3-methyl-4-(methylthio)phenyl) phosphorothioate],
diazinon [O,O-diethyl-O-2-isopropyl-6-methylpyrimidin-4-ylphosphorothioate]
chlorpyriphos [O,O-diethyl-O-3,5, 6-trichloro-2-pyridyl phosphorothioate],
acephate [O,S-dimethylacetyl phosphoramidothioate], methidathione [S-2,3-dihydro-5-methoxy-2-oxo-1,3,4-thiadiazole-3-ylmethyl O,O-dimethylphosphorodithioate],
disulfoton [O,O-diethyl S-2-ethylthioethyl phosphorothioate],
DDVP [2,2-dichlorovinyl dimethylphosphate],
sulprofos [O-ethyl O-4-(methylthio) phenyl S-propyl phosphorodithioate],
cyanophos [O-4-cyanophenyl O,O-dimethylphosphorothioate],
dioxabenzofos [2-methoxy-4H-1,3,2-benzodioxaphosphorin-2-sulfide],
dimethoate [O,O-dimethyl-S-(N-methylcarbamoylmethyl) dithiophosphate],
phenthoate [ethyl 2-dimethoxyphosphinothioylthio(phenyl) acetate],
malathion [diethyl (dimethoxyphosphinothioylthio) succinate],
trichlorfone [dimethyl (2,2,2-trichloro-1-hydroxyethyl) phosphonate],
azinphos-methyl [S-(3,4-dihydro-4-oxo-1,2,3-benzotriazine-3-ylmethyl) O,O-dimethyl phosphorodithioate],
monocrotophos [dimethyl-(E)-1-methyl-2-(methylcarbamoyl) vinyl phosphate], and
ethion [O,O,O',O'-tetraethyl S,S'-methylenebis (phosphorodithioate)].

Other examples are carbamate compounds such as BPMC [2-sec-butyl phenylmethylcarbamate],
benfuracarb [ethyl N-(2.3-dihydro-2,2-dimethylbenzofuran-7-yloxycarbonyl (methyl)aminothio]-N-isopropyl-β-alaninate],
propoxur [2-isopropoxyphenyl N-methylcarbamate],
carbosulfan [2,3-dihydro-2,2-dimethyl-7-benzo [b]furanyl N-dibutylaminothio-N-methyl carbamate],
carbaryl [1 -naphthyl-N-methylcarbamate],
methomyl [S-methyl-N-((methylcarbamoyl)oxy, thioacetoimidate],
ethiofencarb [2-(ethylthiomethyl)phenyl methyl carbamate],
aldicarb [2-methyl-2-(methylthio) propanaldehyde O-(methylcarbamoyioxime)],
oxamyl [N,N-dimethyl-2-methylcarbamoyloxyimino-2-(methylthio)acetamide], and
fenothiocarb [S-4-phenoxybutyl)-N,N-dimethyl-thiocarbarmate].

Other examples include pyrethroid compounds such as
etofenprox [2-(4-ethoxyphenyl)-2-methylpropyl-3-phenoxybenzyl ether],
fenvalerate [(RS)-α-cyano-3-phenoxybenzyl (RS)-2-(4-chlorophenyl)-3-methylbutyrate],
es-fenvalerate [(S)-α-cyano-3-phenoxybenzyl (S)-2-(4-chlorophenyl)-3-methylbutyrate],
fenpropathrin [(RS)-α-cyano-3-phenoxybenzyl 2,2,3,3-tetramethylcyclopropanecarboxylate],
cypermethrin [(RS)-α-cyano-3-phenoxybenzyl (1RS)-cis, trans-3-(2,2-dichlorovinyl)-2,2-dimethylcyclopropanecarboxylate],
permethrin [3-phenoxybenzyl (1RS)-cis,trans-3-(2,2-dichlorovinyl)-2, 2-dimethylcyclopropanecarboxylate],
cyhalothrin [(RS)-α-cyano-3-phenoxybenzyl (Z)-(1RS)-cis-3-(2-chloro-3,3,3-trifluoroprop-1-enyl)-2,2-dimethylcyclopropanecarboxylate],
deltamethrin [(S)-α-cyano-3-phenoxybenzyl (1R)-cis-3-(2, 2-dibromovinyl)-2,2-dimethylcyclopropanecarboxylate],
cycloprothrin [(RS)-α-cyano-3-phenoxybenzyl (RS)-2,2-dichloro-1-(4-ethoxyphenyl)cyclopropanecarboxylate],
fluvalinate [α-cyano-3-phenoxybenzyl N-(2-chloro-α, α, α-trifluoro-p-tolyl)-D-valinate),
bifenthrin [2-methylbiphenyl-3-ylmethyl) (Z)-(1RS)-cis-3-(O-chloro-3,3, 3-trifluoroprop-1-enyl)-2,2-dimethyl-cyclopropanecarboxylate,
2-methyl-2-(4-bromodifluoromethoxyphenyl) propyl (3-phenoxybenzyl) ether,
tralomethrin[(1 R-cis) 3{(1'RS (1',2',2',2'-tetrabromoethyl)}-2,2-dimethylcyclopropanecarboxylic acid (S)-α-cyano-3-phenoxybenzyl ester],
silafluofen [4-ethoxyphenyl {3-(4-fluoro-3-phenoxyphenyl) propyl} dimethylsilane],
d-phenothrin [3-phenoxybenzyl (1R-cis,trans)-chrysantemate],
cyphenothrin [(RS)-α-cyano-3-phenoxybenzyl (1R-cis, trans)-chrysanthemate],
d-resmethrin [5-benzyl-3-furylmethyl (1R-cis,trans)-chrysanthemate],
acrinathrin [(S)-α-cyano-3-phenoxybenzyl (1R-cis (Z))-(2, 2-dimethyl-3-{3-oxo-3-(1,1,1,3,3,3-hexafluoropropyloxy) propenyl}cyclopropane-carboxylate],
cyfluthrin [(RS)-α-cyano-4-fluoro-3-phenoxybenzyl 3-(2,2-dichlorovinyl)-2, 2-dimethylcyclopropanecarboxylate],
tefluthrin [2,3,5,6-tetrafluoro-4-methylbenzyl (1RS-cis(Z))-3-(2,2-chloro-3,3, 3-5 trifluoroprop-1-enyl)-2,2-dimethylcyclopropanecarboxylate],
transfluthrin 12,3,5,6-tetrafluorobenzyl (1R-trans)-3-(2,2-dichlorovinyl)-2, 2-dimethylcyclopropanecarboxylateπ,
tetramethrin [3,4,5,6-tetrahydrophthalimidomethyl (1RS)-cis,trans-chrysanthemate],
allethrin [(RS)-3-allyl-2-methyl-4-oxocyclopent-2-enyl (1 RS)-cis,trans-chrysanthemate],
prallethrin [(S)-2-methyl-4-oxo-3-(2-propynyl) cyclopent-2-enyl(lR)-cis,trans-chrysanthemate],
empenthrin [(RS)-1-ethynyl-2-methyl-2-pentenyl (1R)-cis, trans-chrysanthemate],
imiprothrin [2,5-dioxo-3-(prop-2-ynyl) imidazolidin-1-ylmethyl (1 R)-cis, trans-2,2-dimethyl-3-(2-methylprop-1-enyl)cyclopropane carboxylate],
d-furamethrin [5-(2-propynyl) furfuryl (1 R)-cis,trans-chrysanthemate], and 5-(2-propynyl)-furfuryl 2,2,3,3-tetramethylcyclopropanecarboxylate.

Other examples include thiadiazine derivatives such as buprofezin (2-tert-butylimino-3-isopropyl-5-phenyl-1,3.5-thiadiazinan-4-one),
nitroimidazolidine derivatives such as Imidacloprid (1-(6-chloro-3-pyridylmethyl)-N-nitroimidazolidin-2-ylindenamine], nereistoxin derivatives such as cartap [S.S'-(2-dimethylaminotrimethylene)bis(thiocarbamate)],
thiocyclam [N,N-dimethyl-1,2,3-trithian-5-ylamine] and Bensultap [S,S'-2-dimethylaminotrimethylenedi (benzenethiosulfonate)],
N-cyanoamidine derivatives such as N-cyano-N'-methyl-N'-(6-chloro-3-pyridylmethyl)acetoamidine;
chlorinated hydrocarbons such as endosulfan [6,7,8,9,10,10-hexachloro-1 ,5,5a,6,9,9a-hexahydro-6,9-methano-2,4,3-benzodioxathiepin-3-oxide],
γ-BHC [1,2,3,4,5,6-hexachlorocyclohexane], 1,1-bis (chlorophenyl)-2,2, 2-trichloroethanol, benzoylphenylurea compounds such as chlorofluazuron [1-(3,5-dichloro-4-(3-chloro-5-trifluoromethylpyridine-2-yloxy) phenyl)-3-(2,6-difluorobenzoyl) urea,
teflubenzuron [1-(3,5-dichloro-2,4-difluorophenyl)-3-(2,6-difluorobenzoyl) urea],
and fulphenoxron [1-(4-(2-chloro-4-trifluoromethylphenoxy)-2-fluorophenyl]-3-(2,6-difluorobenzoyl) urea],
formamidine derivatives such as amitraz [N,N'-[(methylamino) dimethylidine] di-2,4-xylidine], chlorodimeform [N'-(4-chloro-2-methylphenyl)-N,N-dimethylmethinimidamide];
thiourea derivatives such as diafenthiuron [N-(2,6-diisopropyl-4-phenoxyphenyl)-N'-tert-butylcarbodiimide];
phenylpyrazole compounds such as bromopropylate [isopropyl 4,4'-dibromobenzilate],
tetradifon [4-chlorophenyl 2,4,5-trichlorophenyl sulfone],
quinomethionate [S,S-6-methylquinoxaline-2,3-diyldithiocarbonate],
propargite [2-(4-tert-butylphenoxy)cyclohexyl prop-2-yl sulfate],
fenbutatin oxide [bis(tris(2-methyl-2-phenylpropyl]tin] oxide, hexythiazox [(4RS,5RS)-5-(4-chlorophenyl)-N-chlorohexyl-4-methyl-2-oxo-1,3-thiazolidine-3-carboxamide],
chlofentezine [3,6-bis(2-chlorophenyl)-1,2,4,5-tetrazine], pyridathioben [2-tert-butyl-5-(4-tert-butylbenzylthio)-4-chloropyridazin-3(2H)-one],
phenypyroxymate [tert-butyl(E)-4-[(1,3-dimethyl-5-phenoxypyrazole-4-yl) methyleneaminotoxymethyl] benzoate],
debphenpyrad [4-N-tert-butylbenzyl)-4-chloro-3-ethyl-1-methyl-5-pyrazol carboxamide];
polynactin complexes including tetranactin, trinactin and dinactin,
milbemectin, avermectin, ivermectin, azadilactin [AZAD], pyrimidifen [5-chloro-N-[12-{4-(2-ethoxyethyl)-2,3-dimethylphenoxy} ethyl]-6-ethylpyrimidine-4-amine,
fipronil [1 H-pyrazole-3-carbonitrile-5-amino-1-{2,6-dichloro-4-(trifluoromethyl) phenyl}-4-{-(trifluoromethyl)sulfinyl}]; methoxaziazone [5-methoxy-3-(2-methoxyphenyl)-1,3,4-oxadiazol-2(3H)-one].

When the present compound is used as an active ingredient of an agent for controlling noxious organisms for agricultural use, its application rate is usually 5 to 500 g per 10 ares. Emulsifiable concentrates, wettable powders and flowables are usually diluted with water to the concentration of 0.1 to 1000 ppm. Granules and dusts are applied as prepared. When the present compound is used as an active ingredient of an agent for controlling noxious organisms, emulsifiable concentrates, wettable powders and flowables for household use are usually diluted with water to the concentration of 0.1 to 1000 ppm. Oil solutions, aerosols, fumigants, smoke formulations, transpiration formulations, fog formulations, ULV formulations, poison baits, etc. are applied as prepared.

The application rate and a concentration of the formulations may be varied, i.e., optionally increased or decreased according to the type of formulation, time, place and method of application, kind of noxious insect, degree of damage and the like.

The following Preparation Examples, Formulation Examples and Test Examples further illustrate the present invention in detail but are not to be construed to limit the scope thereof.

First, Production Examples of the present compound will be described.

PREPARATION EXAMPLE 1

To a mixed solution of 300 mg of (RS)-2-methyl-3-(2,2,2-trifluoroethyl)-4-oxocyclopent-2-en-1-ol, 5 mg of 2,6-di-tert-butyl-4-methylphenol, 185 mg of pyridine, 5 mg of 4-dimethylaminopyridine and 8 ml of dried tetrahydrofuran, 422 mg of (1 R)-trans-3-(2,2-dichlorovinyl)-2,2-dimethylcyclopropanecarboxylic acid chloride was added under ice cooling, and the mixture was further reacted at room temperature for 8 hours. Thereafter, 10 ml of an aqueous 10% ammonia solution was added to the reaction solution, followed by stirring vigorously for 2 hours. The reaction solution was extracted three times with diethyl ether and the layer were combined. Then, the combined ether layer was washed with saturated saline and dried over anhydrous magnesium sulfate, and the solvent was distilled off under reduced pressure. The residue was subjected to silica gel column chromatography (eluent: mixture of n-hexane and ethyl acetate (30:1) containing 0.1% 2,6-di-tert-butyl-4-methylphenol) to give 460 mg of (RS)-2-methyl-3-(2,2,2-trifluoroethyl)-4-oxo-2-cyclopenten-1-yl (1R)-trans-3-(2,2-dichlorovinyl)-2, 2-5 dimethylcyclopropanecarboxylate (compound 5) (yield: 77%).

$n_D^{25}$1.4915 ; $^1$H-NMR (CDCl$_3$, inter standard TMS); δ value (ppm) 1.21 (m, 3H), 1.35 (m, 3H), 1.63 (m, 1H), 2.12 (d, 3H), 2.35 (m, 2H), 2.76 (m, 1H), 3.12 (q, 2H), 5.62 (m, 1H), 5.76 (brd, 0.5H), 5.85 (brd, 0.5H)

PREPARATION EXAMPLE 2

To a mixed solution of 300 mg of (RS)-2-methyl-3-(2,2,2-trifluoroethyl)-4-oxocyclopent-2-en-1-ol, 5 mg of 2,6-di-tert-butyl-4-methylphenol, 185 mg of pyridine, 5 mg of 4-dimethylaminopyridine and 8 ml of dried tetrahydrofuran, 425 mg of 2,2,3,3-tetramethylcyclopropanecarboxylic acid chloride (70% (w/tw) toluene solution) was added dropwise under ice cooling, and the mixture was continuously reacted at room temperature for 6 hours. Thereafter, 10 ml of an aqueous 10% ammonia solution was added to the reaction solution, followed by stirring vigorously for 2 hours. The reaction solution was extracted three times with diethyl ether and the layers were combined. Then, the combined ether layer was washed with saturated saline and dried over anhydrous magnesium sulfate, and the solvent was distilled of f under reduced pressure. The residue was subjected to silica gel column chromatography (eluent: mixture of n-hexane and ethyl acetate (30:1) containing 0.1% 2,6-di-tert-butyl-4-methylphenol) to give 275 mg of (RS)-2-methyl-3-(2,2, 2-trifluoroethyl)-4-oxo-2-cyclopenten-1-yl 2,2,3,3-tetramethylcyclopropanecarboxylate (compound 9) (yield: 56%).

$n_D^{25}$1.4621; $^1$H-NMR (CDCl$_3$, internal standard TMS); δ value (ppm) 1.23 (m, 13H), 2.11 (s, 3H), 2.32 (dd, 1 H), 2.92 (dd, 1 H), 3.10 (q, 2H), 5.73 (brd, 1 H); $^{19}$F-NMR (CDCl$_3$, internal standard CCl$_3$F); δ value (ppm) −64.95 (t, 3F)

PREPARATION EXAMPLE 3

To a mixed solution of 300 mg of (RS)-2-methyl-3-(2,2,2-trifluoroethyl)-4-oxocyclopent-2-en-1-ol, 5 mg of 2,6-di-tert-butyl-4-methylphenol, 183 mg of pyridine and 7 ml of toluene, 270 mg of (1 R)-trans-2,2-dimethyl-3-(2-methyl-1-propenyl)cyclopropanecarboxylic acid chloride was added dropwise under ice cooling, and the mixture was further reacted at room temperature for 8 hours. The reaction solution was poured into a 5% ice-cooled citric acid solution, and extracted three times with diethyl ether. The layers were combined and the combined ether layer was washed in turn with an aqueous saturated sodium bicarbonate and saturated saline. After drying over anhydrous magnesium sulfate, the solvent was distilled off under reduced pressure. The residue was subjected to silica gel chromatography (eluent: mixture of n-hexane and ethyl acetate (30:1) containing 0.1% 2,6-di-tert-butyl-4-methylphenol) to give 330 mg of (RS)-2-methyl-4-oxo-3-(2,2,2-trifluoroethyl)-2-cyclopenten-1 -yl (1 R)-trans-2,2- dimethyl-3-(2-methyl-1-propenyl)cyclopropanecarboxylate (compound 1) (yield: 66%).

$n_D^{25}$ 1.5185; $^1$H-NMR (CDCl$_3$, internal standard TMS); δ value (ppm) 1.17 (m, 3H), 1.39 (m, 3H), 1.42 (m, 1H), 1.70 (m, 6H), 2.12 (m, 4H), 2.35 (m, 1H), 2.92 (m, 1H), 3.10 (q, 2H), 4.91 (m, 1H), 5.71 (brd, 0.5H) 5.82 (brd, 0.5H); $^{19}$F-NMR(CDCl$_3$, internal standard CCl$_3$F); δ value (ppm) −64.93 (t, 3H)

PREPARATION EXAMPLE 4

To a mixed solution of 300 mg of (RS)-2-methyl-3-(2,2,2-trifluoroethyl)-4-oxocyclopent-2-en-1-ol, 5 mg of 2,6-di-tert-butyl-4-methylphenol, 178 mg of pyridine, 5 mg of 4-dimethylaminopyridine and 10 ml of dried tetrahydrofuran, 400 mg of (2S)-2-(4-chlorophenyl)-methylbutanoic acid chloride was added dropwise under ice cooling, and the mixture was further reacted at room temperature for 6 hours. Thereafter, 10 ml of an aqueous 10% ammonia solution was added to the reaction solution, followed by stirring vigorously for 2 hours. The reaction solution was extracted three times with diethyl ether and the layers were combined. Then, the combined ether layer was washed with saturated saline and dried over anhydrous magnesium sulfate, and the solvent was distilled off under reduced pressure. The residue was subjected to silica gel column chromatography (eluent: mixture of n-hexane and ethyl acetate (30:1) containing 0.1% 2,6-di-tert-butyl-4-methylphenol) to give 450 mg of (RS)-2-methyl-3-(2,2,2-trifluoroethyl)-4-oxo-2-cyclopenten-1 -yl (2S)-2-(4-chlorophenyl)-3-methylbutanoate (compound 16) (yield: 78%).

$n_D^{24}$ 1.4989; $^1$H-NMR (CDCl$_3$, internal standard TMS); δ value (ppm) 0.17 (m, 3H), 1.09 (m, 3H), 1.95 (d, 3H), 2.28 (m, 2H), 3.02 (m, 3H), 3.20 (d, 1H), 5.78 (m, 1H), 7.28 (m, 4H); $^{19}$F-NMR −64.91 (t, 3F)

PREPARATION EXAMPLE 5

To a mixed solution of 300 mg of (RS)-2-methyl-3-(2,2,2-trifluoroethyl)-4-oxocyclopent-2-en-1-ol, 5 mg of 2,6-di-tert-butyl-4-methylphenol, 178 mg of pyridine, 5 mg of 4-dimethylaminopyridine and 10 ml of dried tetrahydrofuran, 368 mg of (2S)-2-(4-fluorophenyl)-3-methylbutanoic acid chloride was added dropwise under ice cooling, and the mixture was continuously reacted at room temperature for 6 hours. Thereafter, 10 ml of an aqueous 10% ammonia solution was added to the reaction solution, followed by stirring vigorously for 2 hours. The reaction solution was extracted three times with diethyl ether and the layers were combined. Then, the combined ether layer was washed with saturated saline and dried over anhydrous magnesium sulfate, and the solvent was distilled off under reduced pressure. The residue was subjected to silica gel column chromatography (eluent: mixture of n-hexane and ethyl acetate (30:1) containing 0.1% 2,6-di-tert-butyl-4-methylphenol) to give 400 mg of (RS)-2-methyl-3-(2,2,2-trifluoroethyl)-4-oxo-2-cyclopenten-1-yl (2S)-2-(4-fluorophenyl)-3-methylbutanoate (compound 70) (yield: 73%).

$n_D^{24}$ 1.4819; $^1$H-NMR (CDCl$_3$, internal standard TMS); δ value (ppm) 0.78 (m, 3H), 1.09 (m, 3H), 1.95 (d, 3H), 2.81 (m, 2H), 3.01 (m, 3H), 3.20 (d, 1H), 5.76 (m, 1H), 7.02 (m, 2H), 7.32 (m, 2H); $^{19}$F-NMR (CDCl$_3$, internal standard CCl$_3$F); −115.34 (s, 1 F), −64.91 (t, 3F)

Examples of the present compound are shown in Tables 1 to 4, together with their compound No. (respective substituents of the compound represented by the formula I are shown).

In Tables 1 to 4, R$_3$ is represented by Q$_1$ to Q$_{27}$ described in the formulas XI and XII.

Formula XI

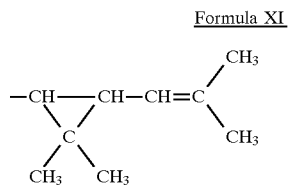

Q$_1$

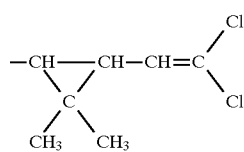

Q$_2$

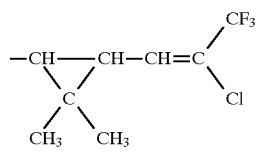

Q$_3$

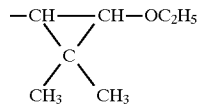

Q$_4$

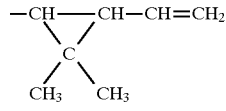

Q$_5$

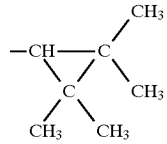

Q$_6$

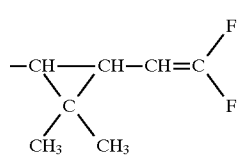

Q$_7$

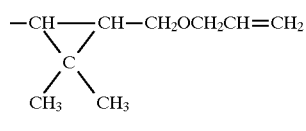

Q$_8$

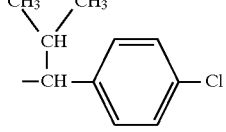

Q$_9$

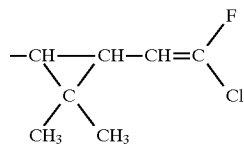

Q$_{10}$

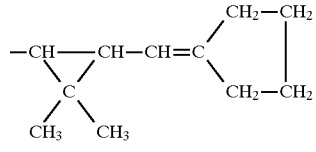

Q$_{11}$

-continued
Formula XI

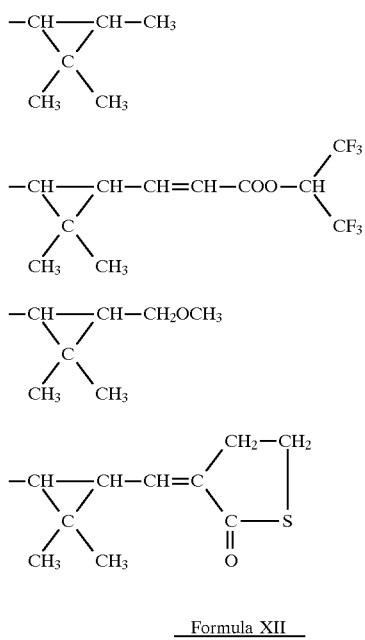

Formula XII

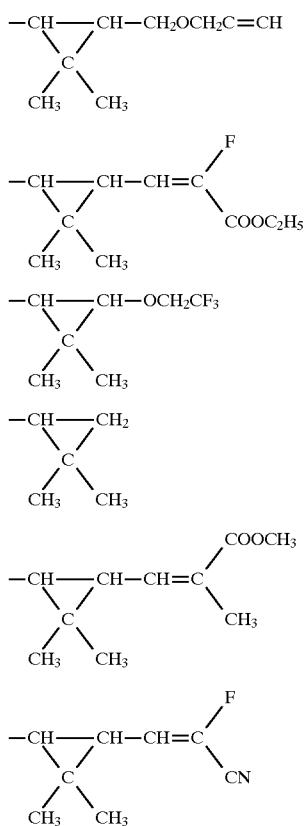

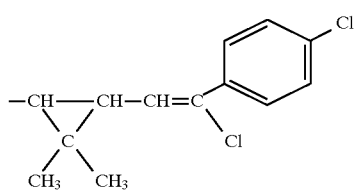

-continued
Formula XII

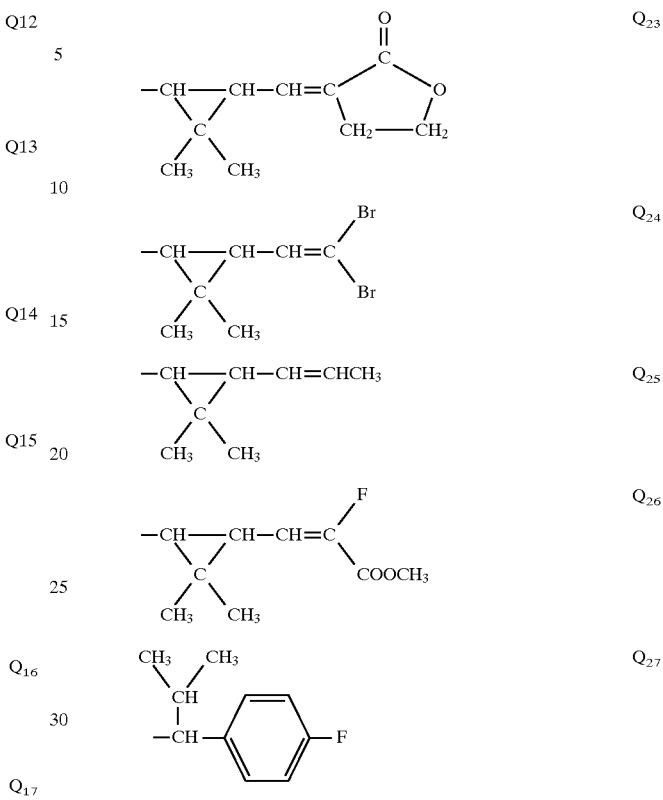

TABLE 1

| Compound No. | $R_1$ | $R_2$ | Optical isomerism of alcohol moiety | $R_3$ | Isomerism of $R_3$ |
|---|---|---|---|---|---|
| 1 | $CH_3$ | $CF_3CH_2$ | RS | $Q_1$ | (1R)-trans |
| 2 | H | $CF_3CH(CH_3)$ | RS | $Q_1$ | (1R)-cis, trans |
| 3 | $CH_3$ | $CF_3CF_2$ | RS | $Q_1$ | (1R)-trans |
| 4 | H | $CF_3CH(CH_3)$ | RS | $Q_2$ | (1R)-trans |
| 5 | $CH_3$ | $CF_3CH_2$ | RS | $Q_2$ | (IR)-trans |
| 6 | H | $CF_3CH(CH_3)$ | RS | $Q_3$ | (1RS)-cis (Z) |
| 7 | $CH_3$ | $CF_3CH_2$ | RS | $Q_4$ | (1RS)-cis, trans |
| 8 | $CH_3$ | $CF_3CH_2$ | RS | $Q_5$ | (1R)-trans |
| 9 | $CH_3$ | $CF_3CH_2$ | RS | $Q_6$ | — |
| 10 | $CH_3$ | $CF_3CH_2$ | RS | $Q_7$ | (1RS)-trans |
| 11 | $CH_3$ | $CF_3CF_2$ | RS | $Q_2$ | (1R)-trans |
| 12 | H | $CF_3CH(CH_3)$ | RS | $Q_6$ | — |
| 13 | $CH_3$ | $CF_3CH_2$ | RS | $Q_8$ | (1R)-trans |
| 14 | $CH_3$ | $CF_3CF_2$ | RS | $Q_7$ | (1RS)-trans |
| 15 | $CH_3$ | $FCH_2CH_2$ | RS | $Q_1$ | (1R)-trans |
| 16 | $CH_3$ | $CF_3CH_2$ | RS | $Q_9$ | (S) |
| 17 | $CH_3$ | $CF_3CH_2$ | RS | $Q_{10}$ | (1R)-trans (EZ) |
| 18 | $CH_3$ | $CF_3CH_2$ | RS | $Q_{11}$ | (1R)-trans |
| 19 | $CH_3$ | $CF_3CF_2$ | RS | $Q_5$ | (1R)-trans |

TABLE 2

| 20 | $CH_3$ | $FCH_2CH_2$ | RS | $Q_5$ | (1R)-cis |
| 21 | $CH_3$ | $FCH_2CH_2$ | RS | $Q_1$ | (1R)-cis, trans |
| 22 | $CH_3$ | $FCH_2CH_2$ | RS | $Q_7$ | (1R)-trans |
| 23 | $CH_3$ | $CF_3CH_2CH_2$ | RS | $Q_1$ | (1R)-trans |
| 24 | $CH_3$ | $CF_3CH_2$ | RS | $Q_{12}$ | (1R)-trans |
| 25 | $CH_3$ | $CF_3CH_2$ | RS | $Q_{13}$ | (1R)-cis (E) |
| 26 | $CH_3$ | $CF_3CH_2$ | RS | $Q_{14}$ | (1R)-trans |
| 27 | $CH_3$ | $CF_3CF_2$ | RS | $Q_6$ | — |
| 28 | $CH_3$ | $CF_3CH_2$ | RS | $Q_{15}$ | (1R)-cis (E) |

TABLE 2-continued

| 29 | CH$_3$ | CF$_3$CF$_2$ | RS | Q$_{10}$ | (1RS)-trans (E/Z) |
| 30 | CH$_3$ | CF$_3$CH$_2$ | RS | Q$_{16}$ | (1R)-trans |
| 31 | CH$_3$ | CF$_3$CH$_2$ | RS | Q$_{17}$ | (1R)-cis (E) |
| 32 | CH$_3$ | CF$_3$CH$_2$ | RS | Q$_1$ | (1R)-cis, trans |
| 33 | CH$_3$ | CF$_3$CF$_2$ | RS | Q$_1$ | (1R)-cis, trans |
| 34 | CH$_3$ | F$_2$CHCH$_2$ | RS | Q$_{10}$ | (1R)-trans (E/Z) |
| 35 | CH$_3$ | CF$_3$CH$_2$ | RS | Q$_{18}$ | (1RS)-cis, trans |
| 36 | CH$_3$ | FCH$_2$CH$_2$ | RS | Q$_2$ | (1R)-trans |
| 37 | CH$_3$ | F$_2$CHCH$_2$ | RS | Q$_1$ | (1R)-cis, trans |

TABLE 3

| 38 | CH$_3$ | CF$_3$CH$_2$ | RS | Q$_{19}$ | (1R)-cis (E) |
| 39 | CH$_3$ | CF$_3$CH$_2$ | RS | Q$_{20}$ | (1R)-cis (E) |
| 40 | CH$_3$ | CF$_3$CH$_2$ | RS | Q$_{21}$ | (1R)-cis (E) |
| 41 | CH$_3$ | CF$_3$CH$_2$ | RS | Q$_{22}$ | (1R)-trans (Z) |
| 42 | CH$_3$ | CF$_3$CH$_2$ | RS | Q$_{23}$ | (1R)-cis (E) |
| 43 | CH$_3$ | F$_2$CHCH$_2$ | RS | Q$_6$ | — |
| 44 | CH$_3$ | FCH$_2$CH$_2$ | RS | Q$_6$ | — |
| 45 | CH$_3$ | CF$_3$CH$_2$ | RS | Q$_3$ | (1RS)-cis (E) |
| 46 | CH$_3$ | F$_2$CHCH$_2$ | RS | Q$_2$ | (1R)-trans |
| 47 | CH$_3$ | CF$_3$CH$_2$CH$_2$ | RS | Q$_6$ | — |
| 48 | CH$_3$ | CF$_3$CF$_2$ | RS | Q$_3$ | (1RS)-cis (Z) |
| 49 | CH$_3$ | CF$_3$CF$_2$ | RS | Q$_{12}$ | (1R)-trans |
| 50 | CH$_3$ | F(CH$_2$)$_3$ | RS | Q$_1$ | (1R)-trans |
| 51 | CH$_3$ | F$_2$CHCH$_2$CH$_2$ | RS | Q$_1$ | (1R)-trans |
| 52 | CH$_3$ | F(CH$_2$)$_3$ | RS | Q$_6$ | — |
| 53 | CH$_3$ | F$_2$CHCH$_2$CH$_2$ | RS | Q$_6$ | — |
| 54 | CH$_3$ | CF$_3$CH$_2$CH$_2$ | RS | Q$_2$ | (1R)-trans |
| 55 | CH$_3$ | F$_2$CHCH$_2$ | RS | Q$_7$ | (1R)-trans |
| 56 | CH$_3$ | CF$_3$CH$_2$CH$_2$ | RS | Q$_{10}$ | (1R)-trans (E/Z) |
| 57 | CH$_3$ | CF$_3$CH$_2$CH$_2$ | RS | Q$_7$ | (1R)-trans |
| 58 | CH$_3$ | F$_2$CHCH$_2$ | RS | Q$_5$ | (1R)-trans |
| 59 | H | CF$_3$CH(CH$_3$) | RS | Q$_{12}$ | (1R)-trans |

TABLE 4

| 60 | H | CF$_3$CH(CH$_3$) | RS | Q$_1$ | (1R)-cis, trans |
| 61 | CH$_3$ | CF$_3$CF$_2$CF$_2$ | RS | Q$_6$ | — |
| 82 | CH$_3$ | F(CH$_2$)$_3$ | RS | Q$_2$ | (1R)-trans |
| 63 | CH$_3$ | CF$_3$CH$_2$ | RS | Q$_{24}$ | (1R)-cis |
| 64 | CH$_3$ | CF$_3$CH$_2$ | RS | Q$_{25}$ | (1R)-trans (E/Z) |
| 65 | CH$_3$ | CF$_3$CF$_2$ | RS | Q$_{13}$ | (1R)-cis (Z) |
| 66 | CH$_3$ | CF$_3$CH$_2$CH$_2$ | RS | Q$_5$ | (1R)-trans |
| 67 | CH$_3$ | CF$_3$CH$_2$ | RS | Q$_{20}$ | (1R)-trans (E) |
| 68 | CH$_3$ | CF$_3$CH$_2$ | RS | Q$_{17}$ | (1R)-trans (E) |
| 69 | CH$_3$ | CF$_3$CH$_2$ | RS | Q$_{26}$ | (1R)-trans (E) |
| 70 | CH$_3$ | CF$_3$CH$_2$ | RS | Q$_{27}$ | S |
| 71 | CH$_3$ | CF$_3$CF$_2$ | RS | Q$_{24}$ | (1R)-cis |
| 72 | H | CF$_3$CH(CH$_3$) | RS | Q$_{24}$ | (1R)-cis |
| 73 | CH$_3$ | ClCH$_2$CH$_2$ | RS | Q$_2$ | (1R)-trans |
| 74 | CH$_3$ | ClF$_2$CCH$_2$ | RS | Q$_2$ | (1R)-trans |

Next, some physical properties of examples of the present compound will be described.

| Compound No. | | |
|---|---|---|
| 1 | $n_D^{22}$ | 1.5185 |
| 5 | $n_D^{25}$ | 1.4915 |
| 9 | $n_D^{25}$ | 1.4621 |
| 16 | $n_D^{22}$ | 1.4989 |
| 70 | $n_D^{24}$ | 1.4819 |

Next, Production Example of the alcohol compound represented by the formula VII will be described.

Production Example of intermediate

To 98.8 g of ethyl 4,4,4-trifluorobutyrylacetate 250 ml of an aqueous 10% sodium hydroxide solution was added, and the resulting mixture was stirred vigorously for 12 hours. After adjusting the pH of the reaction solution to 7.5 by adding an aqueous 10% sulfuric acid solution, 250 ml of toluene, 2.86 g of sodium bicarbonate and 6.43 g of hydrosulfite were added under a nitrogen flow, followed by heating to 37° C. To the mixture, 90 g of methyl glyoxal was added dropwise over one hour and the reaction was conducted for additional 12 hours. To the reaction solution, 50 g of sodium chloride was added, and the mixture was extracted three time with ethyl acetate. The ethyl acetate layers were combined and, after drying over anhydrous magnesium sulfate, the solvent was distilled off under reduced pressure.

To the residue, 450 ml of an aqueous 5% sodium hydroxide solution was added under ice cooling, and the mixture was stirred vigorously for 5 hours. After adjusting the pH of the reaction solution to 7.3 by adding an aqueous 10% hydrochloric acid solution, the solution was extracted three times with ethyl acetate. The layers were combined and the combined ethyl acetate layer was dried over anhydrous magnesium sulfate, and the solvent was distilled under reduced pressure. The residue was distilled off under reduced pressure to give 45 g of the objective (RS)-2-methyl-3-(2,2,2-trifluoroethyl)- 4-oxocyclopent-2-en-1-ol (b.p. 100-133° C., 0.52 mmHg) (yield: 50%).

$^1$H-NMR (CDCl$_3$, internal standard TMS); δ value (ppm): 2.19 (s, 3H), 2.35 (dd, 1H), 2.85 (dd, 1H), 3.08 (q, 2H), 4.82 (br, 1H); $^{19}$F-NMR (CDCl$_3$, CCl$_3$F inner standard); δ value (ppm): −65.1 (t, 3F)

Next, Production Examples of the compounds [V] to [VIII] shown in the reaction scheme X will be described.

REFERENCE PRODUCTION EXAMPLE
(1) Production Example of compound [V]

To 160 g of ethyl 4,4,4-trifluorobutyrate, a mixed solution of 123 g of potassium hydroxide, 900 ml of methanol and 80 ml of water was added under ice cooling and the mixture was further reacted at room temperature for 12 hours. After the reaction solution was concentrated under reduced pressure, the resulting residue was then partitioned between water and diethyl ether. The ether layer was extracted once with water and the water layer was combined with the aqueous layer which had already been partitioned. After adjusting the pH to about 1 by the addition of an aqueous 10% ice-cooled hydrochloric acid solution, the mixture was extracted three times with diethyl ether. The layers were combined and the combined ether layer was washed twice with saturated saline and dried over anhydrous magnesium sulfate. Then, the solvent was distilled off under reduced pressure to give 131 g of 4,4,4-trifluorobutyric acid (yield: 98%).

$^1$H-NMR (CDCl$_3$, internal standard TMS); δ value (ppm): 2.52 (m, 2H), 2.67 (t, 2H)

(2) Production Example of compound [VI]

To a mixture of 131 g of 4,4,4-trifluorobutyric acid and 1 liter of pentane, 101 ml of oxalyl chloride and 0.1 ml of dimethylformamide were added, and the mixture was heated at reflux for 3 hours. The reaction solution was distilled at normal pressure to give 112 g of 4,4,4-trifluorobutyryl chloride (b.p. 103° C., 760 mmHg) (yield: 76%).

(3) Production Example of compound [VII]

To a mixture of 20.35 g of magnesium (turning) and 148 ml of ethanol, 0.1 ml of carbon tetrachloride was added and heated to 55° C. To the mixture, a mixed solution of 197 ml of ethanol, 700 ml of diethyl ether and 168 g of diethyl malonate was added dropwise over one hour. After 2 hours, the reaction solution was cooled to −5° C. under a nitrogen flow and 112 g of 4,4, 4-trifluorobutyryl chloride was added.

After the temperature was returned to ambient temperature over one hour, the reaction was further conducted for 12 hours. The reaction solution was poured into an aqueous 5% ice-cooled hydrochloric acid, and extracted three times with diethyl ether. The layers were combined and the combined ether layer was washed twice with saturated 20 saline and dried over anhydrous magnesium sulfate. Then, the solvent was distilled off under reduced pressure to give 179 g of 4,4,4-trifluorobutyryl-malonic acid diethyl ester (b.p.: 125°–134° C., 15 mmHg) (yield: 90%). $^1$H-NMR (CDCl$_3$, internal standard TMS); δ value (ppm): 1.32 (t, 3H), 2.50 (m, 2H), 2.95 (t, 2H), 4.29 (q, 2H), 4.50 (s, 1H)

(4) Production Example of compound [VIII]

A mixture of 179 g of 4,4,4-trifluorobutyrylmalonic acid diethyl ester 260 ml of water and 322 mg of paratoluenesulfonic acid was stirred vigorously for 6 hours while heating at reflux for 6 hours. The reaction solution was poured into an aqueous saturated sodium bicarbonate, and extracted three times with diethyl ether. The layers were combined, and the combined ether layer was washed with saturated saline and dried over anhydrous magnesium sulfate. Then, the solvent was distilled off under reduced pressure and the residue was distilled under reduced pressure to give 98.8 g of ethyl 4,4,4-trifluorobutyryl acetate (b.p. 93°–97° C., 15 mmHg) (yield: 74%).

$^1$H-NMR (CDCl$_3$, internal standard TMS); δ value (ppm): 1.28 (t, 3H), 2.45 (m, 2H), 2.96 (t, 2H), 3.48 (s, 2H), 4.22 (q, 2H)

Next, Formulation Examples will be described. Further, all "parts" are by weight and the present compounds are represented by the compound Nos. described in Tables 1 to 4.

Formulation Example 1 Emulsifiable concentrates 20 parts of each of the compounds (1) to (74) are separately dissolved in 65 parts of xylene. Each of the obtained mixtures is mixed with 15 parts of an emulsifier Solpol 3005X (trade name by Toho Kagaku Co., Ltd.), and stirred sufficiently to give 20% emulsifiable concentrate for each compound.

Formulation Example 2 Wettable powders

To 40 parts of each of the compounds (1) to (74), 5 parts of Solpol 3005X (same as above) is added, and stirred sufficiently. Then, 32 parts of Carplex #80 (trade name by Shionogi Seiyaku Co., Ltd, synthetic hydrated siliconoxide fine powder) and 23 parts of 300-mesh diatomaceous earth are added to the mixture, which is stirred with a mixer to give 40% emulsifiable concentrate for each compound.

Formulation Example 3 Granules 1.5 parts of each of the compounds (1) to (74) is sufficiently mixed with 98.5 parts of AGSORBLVM-MS 24/48 (granular carrier of calcined montmorillonite having a particle diameter of 24 to 48 meshes, manufactured by OIL DRI Co.) to give 1.5% granule for each compound.

Formulation Example 4 Microcapsules 10 parts of each of the compounds (1) to (74) is sufficiently mixed with 10 parts of phenylxylylethane and 0.5 part of Sumijule L-75 (tolylene diisocyanate manufactured by Sumitomo Bayer Urethane Co., Ltd.) and the mixture is added in 20 parts of an aqueous 10% solution of gum arabic, followed by stirring with a homomixer to give an emulsion of 20 µm in average particle size. Then, 2 parts of ethyleneglycol are added to the emulsion and the mixture is reacted in a hot bath at 60° C. for 24 hours to give a micro-capsule slurry.

On the other hand, 0.2 part of Xanthan gum and 1.0 part of Veegum R (aluminum magnesium silicate manufactured by Sanyo Kasei Co., Ltd.) are dispersed in 56.3 parts of deionized water to give a thickener solution.

42.5 parts of the above microcapsule slurry is mixed with 57.5 parts of the thickener solution to give 10% microcapsule for each compound.

Formulation Examples 5 Flowables 10 parts of each of the compounds (1) to (74) is sufficiently mixed with 10 parts of phenylxylylethane, and the mixture is added in 20 parts of an aqueous 10% solution of polyethyleneglycol, followed by stirring with a homomixer to give an emulsion of 3 µm in average particle size.

On the other hand, 0.2 part of Xanthan gum, 1.0 part of Veegum R (aluminum magnesium silicate manufactured by Sanyo Kasei Co., Ltd.) are dispersed in 58.8 parts of deionized water to give a thickener solution.

40 parts of the above emulsion are mixed with 60 parts of the thickener solution to give 10% flowable for each compound.

Formulation Example 6 Dusts 5 parts of each of the compounds (1) to (74) is separately mixed with 3 parts of Carprex #80 (same as above), 0.3 part of PAP and 91.7 parts of 300 mesh talc, and each of the obtained mixture is stirred with a mixer to give 5% dust for each compound.

Formulation Example 7 Oil solutions 0.1 part of each of the compounds (1) to (74) is separately dissolved in 5 parts of dichloromethane, and each of the solution is mixed with 94.9 parts of deodorized kerosene to give 1.0% oil solution for each compound.

Formulation Example 8 Oil-based aerosol

One part of each of the compounds (1) to (74), 5 parts of dichloromethane are dissolved in 34 parts of deodorized kerosene, and an aerosol vessel is filled with the solution. Then, the vessel is equipped with a valve, through which 60 parts of a propellant (liquefied petroleum gas) are charged under pressure to give an oil-based aerosol for each compound.

Formulation Example 9 Water-based aerosol An aerosol vessel is filled with 50 parts of pure water and a mixture of 0.6 part of each of the compounds (1) to (74), 5 parts of xylene, 3.4 parts of deodorized kerosene and 1 part of an emulsifier (ATMOS 300 (trade name by Atlas Chemical Co.)). Then, the vessel is equipped with a valve, through which 40 parts of a propellant (liquefied petroleum gas) are charged under pressure to give a water-based aerosol for each compound.

Formulation Example 10 Mosquito-coils 0.3 part of each of the compounds (1) to (74) dissolved in 20 ml of acetone, and the solution is mixed uniformly with 99.7 g of a carrier for mosquito-coil (prepared by mixing a flour of Machilus thunbergii Sieb. et Zucc., a pyrethrum marc and a wood flour in a proportion of 4:3:3) with stirring. Then, 120 ml of water is added to the mixture, which is kneaded sufficiently, molded and dried to give a mosquito-coil of each compound.

Formulation Example 11 Mosquito-mat for electric heating fumigation 0.8 g of each of the compounds (1) to (74) and 0.4 g of piperonyl butoxide are each dissolved in acetone to make 10 ml of a solution. A substrate for the mat of electric heating formulations having a size of 2.5 cm×1.5 cm×0.3 cm in thickness (prepared by forming a fibrillated mixture of cotton linter and pulp into a sheet) is impregnated uniformly with 0.5 ml of the solution to give a mosquito-mat for electric heating fumigation of each compound.

Formulation Example 12 Solutions for electric heating fumigation 3 parts of each of the compounds (1) to (74) is separately dissolved in 97 parts of deodorized kerosene, and the solution was charged in a vessel made of vinyl chloride. Then, a core for absorbing solution (prepared by solidifying inorganic powder using a binder, followed by sintering), of which top part can be heated with a heater, is inserted to give a solution for electric heating fumigation of each compound.

Formulation Example 13 Heating smoke formulations 100 mg of each of the compounds (1) to (74) is separately dissolved in a suitable amount of acetone, and a porous ceramic plate having a size of 4.0 cm ×4.0 cm x 1.2 cm in thickness is impregnated with the resulting solution to give heating smoke formulation of each compound.

Formulation Example 14 Volatile agent

One hundred μg of each of the compounds (1) to (74) is separately dissolved in a suitable amount of acetone and the solution is uniformly applied on a filter paper having a size of 2 cm×2 cm×0.3 mm in thickness, and then acetone is air-dried to give a volatile agent of each compound.

Formulation Example 15 Mite-repellent sheet

A filter paper is impregnated with an acetone solution of each of the compounds (1) to (74) so that the amount of the compound to be impregnated is 1 g/m², and acetone is air-dried to give a mite-repellent sheet of each compound.

The following Test Examples illustrate that the present compounds are useful as an active ingredient of an agent for controlling noxious organisms. Further, the present compounds are shown by the compound Nos. in Tables 1 to 4 and the compound [(RS)-isomer on the alcohol side, (1 R)-cis, trans-isomer on the acid side] used for comparison is shown by the symbols in Table 5.

Test Example 2 Insecticidal test against larvae of *Nilaparvata lugens*

A rice stalk (about 5 cm in length) was dipped in an aqueous diluted solution of an emulsifiable concentrate (500 ppm) of the test compound prepared according to Formulation Example 1 for 1 minute. After air drying, the rice stalk was placed in a polyethylene cup of 5.5 cm in diameter wherein a filter paper containing water (1 ml) (5.5 cm in diameter) is put on the bottom. Then, about 30 larvae of *Nilaparvata lugens* were set free in the cup. After six days, the survival of larvae was examined to determine the mortality. The effect was evaluated according to the following criteria.

a: No survival larvae are observed.

b: Five survival larvae or less are observed.

c: Six survival larvae or more are observed.

The results are shown in Table 7.

TABLE 7

| Compound No. | Judgment of effect |
| --- | --- |
| 1 | a |
| 5 | a |
| 9 | a |
| Emulsifiabie concentrate containing no active ingredient | c |

TABLE 5

| Symbol of chemical structural | Compound formula | Remarks |
| --- | --- | --- |
| A | | d-Allethrin (commercially available insecticide) |

Test Example 1 Insecticidal test against larvae of *Spodoptera litura*

An emulsifiable concentrate was prepared from the test compound according to Formulation Example 1. Then, 13 g of an artificial diet for *Spodoptera litura*, prepared in a polyethylene cup having a diameter of 11 cm in advance, was impregnated with 2 ml of a solution of the emulsifiable concentrate diluted with water (500 ppm). Ten fourth instar larvae of *Spodoptera litura* were set free in the cup. After six days, the survival of larvae was examined to determine the mortality. The results are shown in Table 6.

TABLE 6

| Compound No. | Mortality (%) |
| --- | --- |
| 1 | 100 |
| 5 | 100 |
| 9 | 80 |
| Emulsifiable concentrate containing no active ingredient | 0 |

Test Example 3 Insecticidal test against *Musca domestica*

A filter paper of 5.5 cm in diameter was put on the bottom of a polyethylene cup of 5.5 cm in diameter and 0.7 ml of an aqueous diluted solution of an emulsifiable concentrate (500 ppm), prepared from the test compound according to Formulation Example 1 was dropped and, further, about 30 mg of sucrose as a bait was uniformly charged in the cup. Then, 10 female adults *Musca domestica* having low sensitivity to pyrethroid were set free in the cup, and a cap was put on the cup. After one day, the survival of female adults was examined to determine the mortality. The results are shown in Table 8.

TABLE 8

| Compound No. | Mortality (%) |
| --- | --- |
| 1 | 100 |
| 5 | 100 |
| 9 | 90 |
| A | 10 |
| Emulsifiable concentrate containing no active ingredient | 0 |

Test Example 4

Ten adults Blattella germanica (5 male adults and 5 female adults) were released in a polyethylene cup of 9 cm in diameter of which wall surface was applied with vaseline thinly and the cup was covered with a 16-mesh nylon net and, further, the covered up was placed at the bottom of a plastic cylinder (10 cm in inner diameter×37 cm in height). Then, 0.6 ml of each 0.1% (w/w) oil solution of the present compound obtained in Formulation Example 7 was op of the cylinder, using a spray gun at a pressure of the rate of knocked-down adults was examined. The results are shown in Table 9.

TABLE 9

| Compound No. | Knocked-down ratio (%) |
|---|---|
| 5 | 90 |
| 9 | 80 |
| A | 40 |
| Emulsifiable concentrate containing no active ingredient | 0 |

Test Example 5

Ten female adults Culex pipiens pallens were released in a cubic glass chamber having a side of 70 cm(0.34 m$^3$). Then, both ends of a 0.3% (w/w) mosquito coil (1.0 g) of the present compound prepared according to Formulation Example 10 was lit and then placed in the glass chamber. After 8.5 minutes, the rate of knocked-down adults was examined. The results are shown in Table 10.

TABLE 10

| Compound No. | Knocked-down ratio (%) |
|---|---|
| 5 | 70 |
| 9 | 90 |
| A | 10 |

Test Example 6 Insecticidal test against Culex pipiens pallens

An emulsifiable concentrate was made from the test compound according to Formulation Example 1 and the resulting emulsifiable concentrate was diluted with water, and 0.7 ml of the diluted solution was added to 100 ml of deionized water (concentration of active ingredient: 3.5 ppm). Then, 20 heads of final instar larvae of Culex pipiens pallens were set free therein. After one day, the survival of larvae was examined.

The effect was evaluated according to the following criteria.

a: Mortality of 90% or more b: Mortality of 10 or more and less than 90% c: Mortality of less than 10%

The results are own in Table 11.

TABLE 11

| Compound No. | Judgment of effect |
|---|---|
| 1 | a |
| 5 | a |
| 9 | a |
| 16 | a |
| 70 | a |
| Emulsifiable concentrate containing no active ingredient | c |

Test Example 7 Insecticidal test against larvae of Diabrotica undecimpunctata howardi A filter paper of 5.5 cm in diameter was put on the bottom of a polyethylene cup of 5.5 cm in diameter and 1 ml of an aqueous diluted solution of an emulsifiable concentrate (50 ppm) of the test compound prepared according to Formula Example 1 was dropped on the filter paper. Then, about 30 eggs of Diabrotica undecimpunctata howardi were placed on the filter paper and one sprout corn as a bait was charged in the cup. After 8 days, the survival of hatched larvae was examined. The effect was evaluated according to the following criteria.

a: Mortality of 100% b: Mortality of 90% or more and less than 99 % c: Mortality of less than 90%

The results are shown in Table 12.

TABLE 12

| Compound No. | Judgment of effect |
|---|---|
| 1 | a |
| 5 | a |
| 9 | a |
| 16 | a |
| 70 | a |
| Emulsifiable concentrate containing no active ingredient | c |

Test Example 8

0.64 Ml of 0.25% (w/v) solution of the test compound diluted with acetone was dropped on an aluminum dish of which diameter of the bottom part is 7 cm, and the acetone was air-dried. Then, 20 female adults of CSMA Musca domestica were set free in a polyethylene cup (9 cm in diameter×4.5 cm in height) and the top was covered with a 16 mesh nylon net so that the insects do not contact directly with the surface treated with the drug. This cup was placed upside down on the aluminum dish and, after 60 minutes at 25° C., the rate of knocked-down adults was examined. The results are shown in Table 13.

TABLE 13

| Compound No. | Knocked-down ratio (%) |
|---|---|
| 1 | 100 |
| 5 | 90 |
| 9 | 100 |
| A | 0 |
| No treatment | 0 |

Experiment Example 9

A mite-repellent sheet prepared according to Formulation Example 15 was cut into a circle of 4 cm in diameter, and about 50 Dermatophagoides farinae were released on the surface of the filter paper. After one day, the number of mites, which were dead or trapped by an adhesive substance applied on the circumference of the sheet for preventing escape, was counted. The total of the dead or trapped mites was evaluated as an effective controlling value. The results are shown in Table 14.

TABLE 14

| Compound No. | Controlling ratio (%) |
|---|---|
| 1 | 100 |
| 2 | 100 |

TABLE 14-continued

| Compound No. | Controlling ratio (%) |
|---|---|
| 9 | 100 |
| No treatment | 7 |

What is claimed is:

1. An alcohol compound represented by the formula VII:

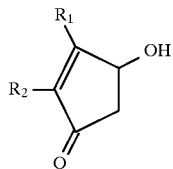

wherein $R_1$ is a methyl group or a hydrogen atom; and $R_2$ is a $C_{2-4}$ alkyl group substituted with two or more fluorine atoms.

2. An alcohol of claim 1, which is (S)-3-(2,2,2-trifluoroethyl)-2-methyl-4-oxo-2-cyclopentenol, (RS)-3-(3,3-difluoropropyl)-2-methyl-4-oxo-2-cyclopentenol, (RS)-3-(pentafluoroethyl)-2-methyl-4-oxo-2-cyclopentenol, (RS)-3-(2,2,2-trifluoroethyl)-2-methyl-4-oxo-2-cyclopentenol, (RS)-3-(3,3,3-trifluoropropyl)-2-methyl-4-oxo-2-cyclopentenol, (RS)-3-(2,2-difluoroethyl)-2-methyl-4-oxo-2-cyclopentenol.

3. An alcohol of claim 1, which is (S)-3-(2,2,2-trifluoroethyl)-2-methyl-4-oxo-2-cyclopentenol.

4. An alcohol of claim 1, which is (RS)-3-(3,3-difluoropropyl)-2-methyl-4-oxo-2-cyclopentenol.

5. An alcohol of claim 1, which is (RS)-3-(pentafluoroethyl)-2-methyl-4-oxo-2-cyclopentenol.

6. An alcohol of claim 1, which is (RS)-3-(2,2,2-trifluoroethyl)-2-methyl-4-oxo-2-cyclopentenol.

7. An alcohol of claim 1, which is (RS)-3-(3,3,3-trifluoropropyl)-2-methyl-4-oxo-2-cyclopentenol.

8. An alcohol of claim 1, which is (RS)-3-(2,2-difluoroethyl)-2-methyl-4-oxo-2-cyclopentenol.

9. An alcohol of claim 1, wherein $R_2$ is selected from the group consisting of 2,2,2-trifluoroethyl, 2,2-difluoroethyl, pentafluoroethyl, 2-fluoroethyl, and 3-fluoropropyl.

* * * * *